(12) United States Patent
Kim et al.

(10) Patent No.: US 10,675,202 B2
(45) Date of Patent: Jun. 9, 2020

(54) LEG REHABILITATION APPARATUS FOR NEUROLOGICAL DISEASE FOR REHABILITATING LEG THROUGH UP/DOWN STRETCHING AND EVERSION/INVERSION STRETCHING FOR MUSCLES

(71) Applicant: Korea Institute of Robot & Convergence, Gyeongsangbuk-do (KR)

(72) Inventors: Dae Hee Kim, Gyeongsangbuk-do (KR); Kap Ho Seo, Gyeongsangbuk-do (KR); Sung Ho Park, Gyeongsangbuk-do (KR); Min Suck Jung, Gyeongsangbuk-do (KR)

(73) Assignee: Korea Institute of Robot & Convergence, Gyeongsangbuk-do (KR)

( * ) Notice: Subject to any disclaimer, the term of this patent is extended or adjusted under 35 U.S.C. 154(b) by 574 days.

(21) Appl. No.: 15/374,687

(22) Filed: Dec. 9, 2016

(65) Prior Publication Data
US 2018/0125736 A1 May 10, 2018

(30) Foreign Application Priority Data
Nov. 9, 2016 (KR) ........................ 10-2016-0148644

(51) Int. Cl.
*A61H 1/00* (2006.01)
*A61H 1/02* (2006.01)
*A61N 1/36* (2006.01)
*A61N 1/04* (2006.01)

(52) U.S. Cl.
CPC ........... *A61H 1/005* (2013.01); *A61H 1/0266* (2013.01); *A61N 1/36003* (2013.01);
(Continued)

(58) Field of Classification Search
CPC ........ A61H 1/00; A61H 1/005; A61H 1/0266; A61H 2201/1246; A61H 1/02;
(Continued)

(56) References Cited

U.S. PATENT DOCUMENTS 4,520,827 A * 6/1985 Wright ................. A61H 1/0255
607/48
6,162,189 A 12/2000 Girone et al.
(Continued)

FOREIGN PATENT DOCUMENTS

CN 102631275 10/2013
CN 105997439 10/2016
(Continued)

*Primary Examiner* — Michael J Tsai
*Assistant Examiner* — Matthew Standard
(74) *Attorney, Agent, or Firm* — IP & T Group LLP

(57) ABSTRACT

An apparatus for rehabilitating a leg includes a base plate; a first plate having a structure such that the first plate is rotatable to lift up a toe part; a second plate having a rotatable structure to enable a sole of the patient to perform inversion and eversion movements and to allow a side surface of the sole to move up and down; a driving device; a power transfer device; and a controller. The first plate includes an outer frame, a first frame for connecting central portions of mutually facing sides of the outer frame to each other to form opening parts at two sides thereof, a second frame, and a rotational part. The second plate is prepared as a pair, and the pair of second plates include second plate bodies disposed in the opening parts, respectively, and connected to the rotational part.

5 Claims, 10 Drawing Sheets

(52) U.S. Cl.
    CPC ........ *A61N 1/36014* (2013.01); *A61H 1/0237*
        (2013.01); *A61H 2001/027* (2013.01); *A61H*
            *2201/1246* (2013.01); *A61H 2201/1436*
                (2013.01); *A61N 1/0452* (2013.01)

(58) Field of Classification Search
    CPC .... A61H 2001/0203; A61H 2001/0207; A61H
            1/0237; A61H 2001/027; A61H 2201/10;
            A61H 2201/12; A61H 2201/14; A61H
                2201/1657; A61H 2205/12; A61N
                1/36003; A61N 1/36014; A61N 1/045
    USPC ................................ 601/23, 27, 22, 97, 104
    See application file for complete search history.

(56) References Cited

U.S. PATENT DOCUMENTS

| | | |
|---|---|---|
| 7,874,968 B2 | 1/2011 | Foucault |
| 8,206,267 B2 | 6/2012 | Holden et al. |
| 8,500,668 B2 | 8/2013 | Siegler et al. |
| 2007/0249476 A1 | 10/2007 | Hill et al. |
| 2010/0262044 A1 | 10/2010 | Siegler et al. |
| 2014/0378876 A1 | 12/2014 | Malosio et al. |
| 2015/0328497 A1* | 11/2015 | Doucot ................. A63B 23/08 482/146 |
| 2018/0110670 A1* | 4/2018 | Saglia ................ A63B 69/0057 |

FOREIGN PATENT DOCUMENTS

| | | |
|---|---|---|
| KR | 101422395 | 7/2014 |
| KR | 101449235 | 10/2014 |

* cited by examiner

LEG REHABILITATION APPARATUS FOR NEUROLOGICAL DISEASE FOR REHABILITATING LEG THROUGH UP/DOWN STRETCHING AND EVERSION/INVERSION STRETCHING FOR MUSCLES

CROSS-REFERENCE TO RELATED APPLICATIONS

This application claims priority under 35 U.S.C. § 119 to Korean Patent Application No. 10-2016-0148644, filed on Nov. 9, 2016 in the Korean Intellectual Property Office, the disclosure of which is incorporated herein by reference in its entirety.

BACKGROUND OF THE INVENTION

1. Field of the Invention

The present invention relates to a leg rehabilitation apparatus for neurological disease, and more particularly, to a leg rehabilitation apparatus for neurological disease which is capable of rehabilitating a diseased muscle around a foot of a neurological patient through up/down stretching and eversion/inversion stretching for muscles.

2. Description of the Related Art

In general, a hip joint and an ankle joint are important for balance and stability. A large range of body wavering is due to the operation of a hip joint and a small range of body wavering is mainly due to the operation of an ankle joint. Specifically, the balance control ability and muscular strength of an old man is reduced as the age of an old man is increase. It has been reported that the loss of sense of balance is concerned with the deterioration of ankle muscular strength and dynamic ankle stability is greatly deteriorated as the age is increased.

Although the ankle joint has a function of controlling the movement and damage caused by a foot, the ankle joint is injured easily and structurally. For example, when toes are oriented downwardly, a sole is dynamically bent, a rear portion of an ankle bone is introduced between a shinbone and a fibula, so that a space in which an excessive motion may occur is generated, thereby frequently causing ankle damage.

In addition, ankle ligament damage is most frequently caused in an ankle joint, so that most injuries concerned to an ankle joint are ankle ligament injuries. The ankle ligament injury is mainly caused due to an inversion sprain. The anterior talofibular ligament, which has a function of preventing an ankle bone from being dislocated forwardly, is the weakest among three outer ankle ligaments, so that damage may occur at inversion and pantar flexions and an internal version motion.

In addition, as the ankle joint is aged, the muscular strength and the kinematic function of the ankle joint is weakened, so that damage such as injury from a fall may occurs. Thus, it is expected that the demand for rehabilitation apparatus by the patients suffering from a stroke and injured in varicose veins, calf muscles and lumbar together with the increase of the population of old people.

Meanwhile, there has been disclosed an automatic crural muscle lengthening exercise apparatus in Korean Patent Registered No. 10-1449235. According to the automatic crural muscle lengthening exercise apparatus, a foot fixing part is repeatedly rotatable while being automatically reciprocated in the normal range of dorsiflexion and plantarflexion of an ankle joint, such that the ankle joint and leg muscles around the ankle joint maintain and acquire the range of a normal joint movement and a muscle length through constant force and speed. Thus, according to Korean Patent Registered No. 10-1449235, the normal movement range of an ankle joint may be maintained and the ankle joint may be prevented from being modified while the tension and spasticity of muscles are reduced.

However, in case of a neurological patient, although eversion/inversion symptoms may occur while muscles are stiffened, the apparatus disclosed in Korean Patent Registered No. 10-1449235 cannot provide any rehabilitation treatments to the neurological patient.

SUMMARY OF THE INVENTION

To solve the problems described above, one objective of the present invention is to provide a leg rehabilitation apparatus which is capable of rehabilitating a diseased muscle around a foot of a neurological patient through up/down stretching and eversion/inversion stretching for muscles.

Another objective of the present invention is to provide a leg rehabilitation apparatus which is capable of providing electrical stimulation and/or muscle vibration treatment together with stretching treatment.

To achieve the objectives described above, according to one aspect of the present invention, there is provided an apparatus for rehabilitating a leg, which includes: a base plate (100) for supporting a patient; a first plate (400) installed to the base plate (100) and having a structure such that the first plate is rotatable to lift up a toe part; a second plate (500) installed inside the first plate (400) and having a rotatable structure to enable a sole of the patient to perform inversion and eversion movements and to allow a side surface of the sole to move up and down; a driving unit (A) coupled to the first and second plates (400 and 500) to drive the first and second plates (400 and 500); a power transfer unit (T) coupled to the first and second plates (400 and 500) and the driving unit (A) to transfer power of the driving unit (A) to the first and second plates (400 and 500); and a control unit (CON) connected to the driving unit (A) to control the driving unit (A) to stretch an ankle and the sole. The first plate (400) includes an outer frame (430) having a hollow rectangular shape, a first frame (410) for connecting central portions of mutually facing sides of the outer frame (430) to each other to form opening parts (O) at two sides thereof, a second frame (420) extending from one side of the first frame (430) toward two sides of the first plate (400) in an orthogonal direction to the one side of the first frame (430) and making contact with an inside of the outer frame (430), and a rotational part (440) provided at one side of the first frame (410) to rotate the second plate (500). The second plate (500) is prepared as a pair, and the pair of second plates (500) include second plate bodies (510) disposed in the opening parts (O) formed at the two sides of the first frame (410), respectively, and connected to the rotational part (440). The rotational part (440) includes a hinge (441) fixed to the first frame (410) and a fixing bar (442) rotatably coupled to the hinge (441). The second plate bodies (510) are fixed to the fixing bar (442).

Preferably, the apparatus further includes an electrical stimulation generating unit (700) connected to the control unit (CON) to apply electrical stimulation to a muscle of the leg under control of the control unit (CON).

The power transfer unit (T) includes a second power transfer unit (200) coupled to two ends of the second plate (500) to rotate the two ends of the second plate (500) about the first frame (410) of the first plate (400), and a first power transfer unit (300) coupled to the first plate (400) to operate the first plate (400). The driving unit (A) includes a second driving unit (A2) coupled to the second power transfer unit (200) to supply forward/backward power to the second power transfer unit (200) and a first driving unit (A1) coupled to the first power transfer unit (300) to supply forward/backward power to the first power transfer unit (300).

The second power transfer unit (200) includes a moving bar (210) moving forward to or backward from the second plate (500) by the second driving unit (A2); a fixing bar (230) disposed in front or rear of the moving bar (210) and fixed to the base plate (100); a first link (2500 having one side rotatably provided to the fixing bar (230); a second link (240) having one side rotatably provided to the moving bar (210), and an opposite side rotatably provided to the first link (250); and a third link (260) having one side rotatably provided to a hinge (270) provided to the second plate (500), and an opposite side rotatably provided to the first link (250).

The second power transfer unit (200) further includes a moving bridge (220) installed to the moving bar (210) to interwork with the moving bar (210), and a guide bar (290) fixed to the base plate (100) to guide a movement of the moving bridge (220), the moving bridge (220) comprises support brackets (222) each provided outside two side ends of the moving bar (210) in a plate shape, and a bridge body (221) connected between the support brackets (222) and disposed at an upper side of the moving bar (210), and the guide bar (290) is disposed on the base plate (100) in a direction through which the moving bar (210) moves and is received in the support bracket (222) such that the guide bar (290) is coupled to the support bracket (222).

The first power transfer unit (300) includes: a moving block (320) moving forwardly or backwardly toward the second plate (500) by the first driving unit (A1); a shaft (340) provided to the moving block (320) and disposed in a direction orthogonal to the moving direction of the first driving unit (A1); a connecting unit (310) having one side which is rotatably provided to the shaft (340) and an opposite side fixed to a low end of an outer frame (430) of the first plate (400); and a support bracket (330) having one side fixed to the base plate (100) and an opposite side rotatably provided to a hinge (350) installed to the second frame (420) of the first plate (400).

According to the present invention, rehabilitating a diseased muscle around a foot of a neurological patient may be treated through up/down stretching and eversion/inversion stretching for muscles.

BRIEF DESCRIPTION OF THE DRAWINGS

The above and other objectives, features and other advantages of the present invention will be more clearly understood from the following detailed description when taken in conjunction with the accompanying drawings, in which.

DETAILED DESCRIPTION OF THE INVENTION

Figure 1:
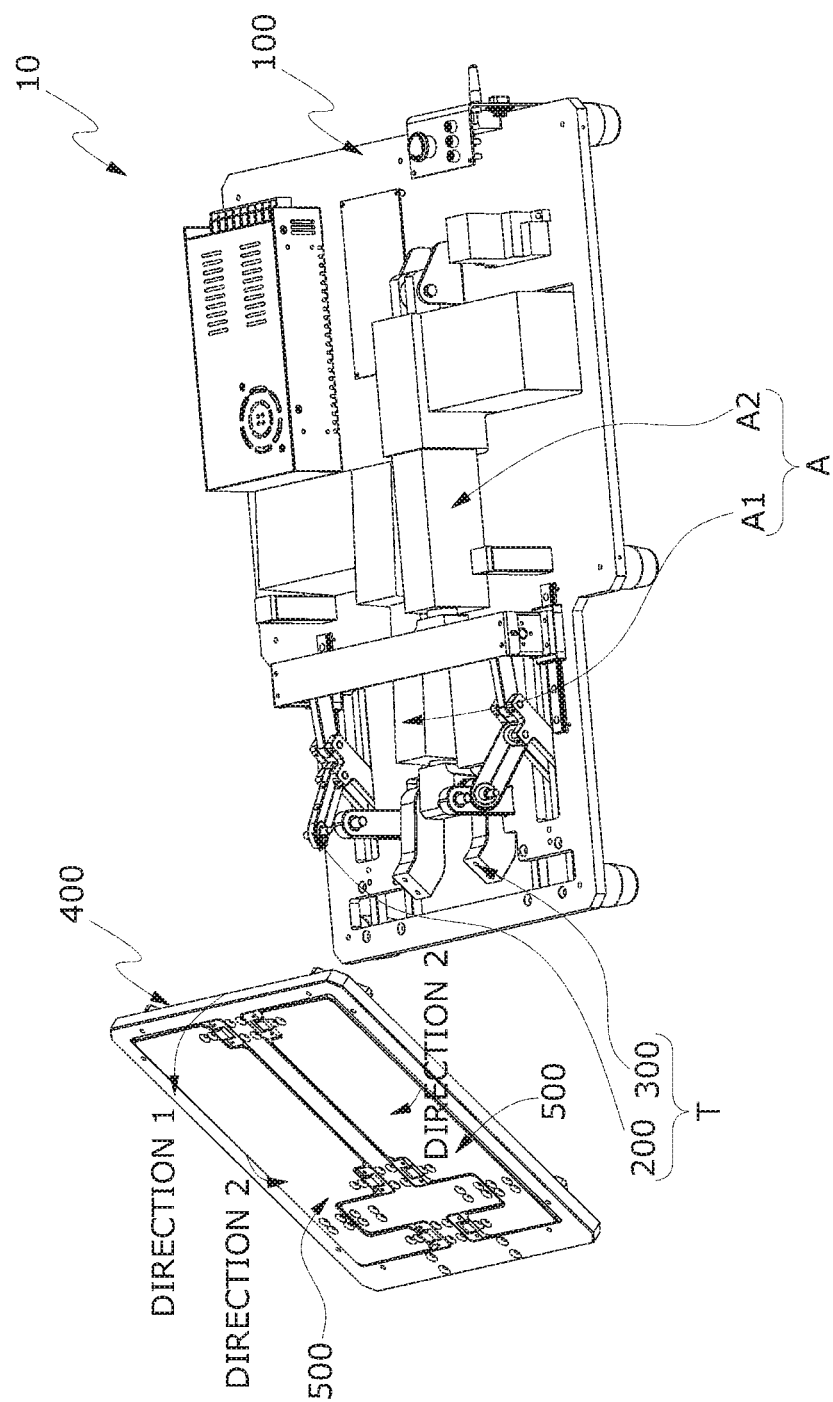
FIG. 1 is a perspective view showing a leg rehabilitation apparatus according to an embodiment of the present invention.

Hereinafter, a preferable embodiment of the present invention will be described with reference to the accompanying drawings. In the drawings, the same elements will be assigned with the same reference numerals and the size of each element may be exaggerated for the purpose of convenience or clarity. Meanwhile, the embodiments described below are only exemplary, and it will be possible to modify the embodiments.

Although terms like a first and a second are used to describe various components, the components are not limited to the terms. The terms are used only to differentiate one component from another one.

The terms of a singular form may include plural forms unless referred to the contrary. In this present invention, the term of "include" implies that elements are further included but does not exclude any other elements.

In addition, in the following description, terms such as "unit" and "module" indicate a unit for processing at least one function or operation, wherein the unit and the block may be embodied as hardware or software or embodied by combining hardware and software.

As shown in FIG. 1, an apparatus 10 for rehabilitating a leg according to an embodiment of the present invention includes a base plate 100 for supporting a patient, a first plate 400 installed to the base plate 100 and having a structure such that the first plate 400 is shaft rotatable to lift up a toe part, and a second plate 500 installed inside the first plate 400 to enable a sole of the patient to perform inversion and eversion movements and having a structure such that the second plate 500 is shaft rotatable to lift up a side surface of the sole.

The first and second plates 400 and 500 are driven by a driving unit A which is coupled to the first and second plates 400 and 500. A power transfer unit T is coupled to the first and second plates 400 and 500 and the driving unit A to transfer the power of the driving unit A to the first and second plates 400 and 500. In this case, the apparatus includes a control unit CON connected to the driving unit A to control the driving unit A to stretch an ankle and the sole, and an electrical stimulation generating unit 700 connected to the control unit CON to apply electrical stimulation to a muscle of the leg under control of the control unit CON (see FIG. 8).

The first plate 400 is rotated in direction 1 by the driving unit A and the toe part of the sole placed on the first plate 400 moves up or down so that the ankle may be rehabilitated. The second plate 500 is rotated in direction 2 by the driving unit A to enable the side surface of the sole to move up or down. Thus, it is possible to allow the sole of a patient to perform inversion and eversion movements.

The first and second plates 400 and 500 will be described with reference to FIGS. 2A and 2B. The first plate 400 includes an outer frame 430 having a hollow rectangular shape, and a first frame 410 for connecting central portions of mutually facing sides of the outer frame 430 to each other. An inner space of the outer frame 430 is divided into space parts O by the first frame 410, which are formed at both sides of the first frame 410. The second frame 420 extends to an inner side surface of the outer frame 430.

Figure 2A:
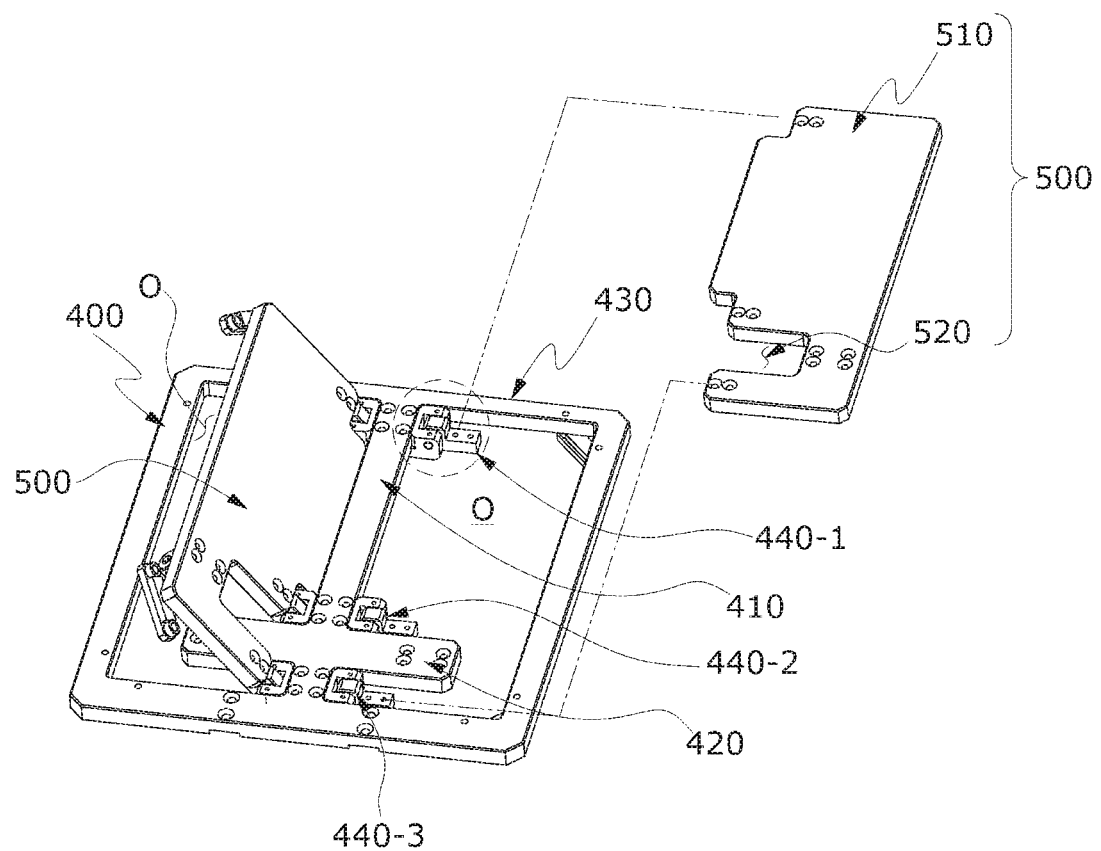
FIGS. 2A and 2B are exploded perspective views showing the first and second plates of leg rehabilitation apparatus according to an embodiment of the present invention.
Figure 2B:
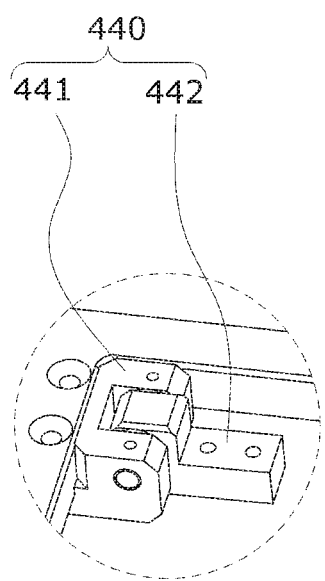

In the case of the embodiment shown in FIGS. 2A 2B, the first frame 410 is formed in the vertical direction in the drawing. The second frame 420 extends in a horizontal direction at a low portion of the drawing. The second plate 500 is provided in the spaces O formed left and right of the first frame 410.

A rotational part 440 is provided at one side of the first frame 410 to rotate the second plate 500, and a plurality of rotational parts 440-1, 440-2 and 440-3 may be provided. The rotational part 440 includes a hinge 441 fixed to the first frame 410 and a fixing bar 442 rotatably coupled to the hinge 441. The fixing bar 442 may be rotatably pin-coupled to the hinge 441.

The second plate 550 is provided to the fixing bar 442. The second plate 550 is prepared as a pair, and the pair of second plates 500 include second plate bodies 510 which are disposed to the opening parts O formed at both sides of the first frame 410, respectively. Each of the second plate bodies 510 is concaved to form a space part 520 in which the second frame 420 is disposed.

As shown in FIG. 1, the first and second plates 400 and 500 are driven by the power transfer unit T and power is transferred from the driving unit A to the power transfer unit T.

The power transfer unit T includes a second power transfer unit 200 coupled to two ends of the second plate 500 to rotate the two ends of the second plate 500 about the first frame 410 of the first plate 400, and a first power transfer unit 300 coupled to the first plate 400 to operate the first plate 400.

The driving unit A includes a second driving unit A2 coupled to the second power transfer unit 200 to supply forward/backward power to the second power transfer unit 200 and a first driving unit A1 coupled to the first power transfer unit 300 to supply the forward/backward power to the first power transfer unit 300.

That is, the second plate 500 is drive in direction 2 by the forward/backward power generated from the second driving unit A2 and transferred through the second power transfer unit 200 thereto. The first plate 400 is driven by the forward/backward power generated from the first driving unit A1 and transferred through the first power transfer unit 300 thereto.

Figure 3A:
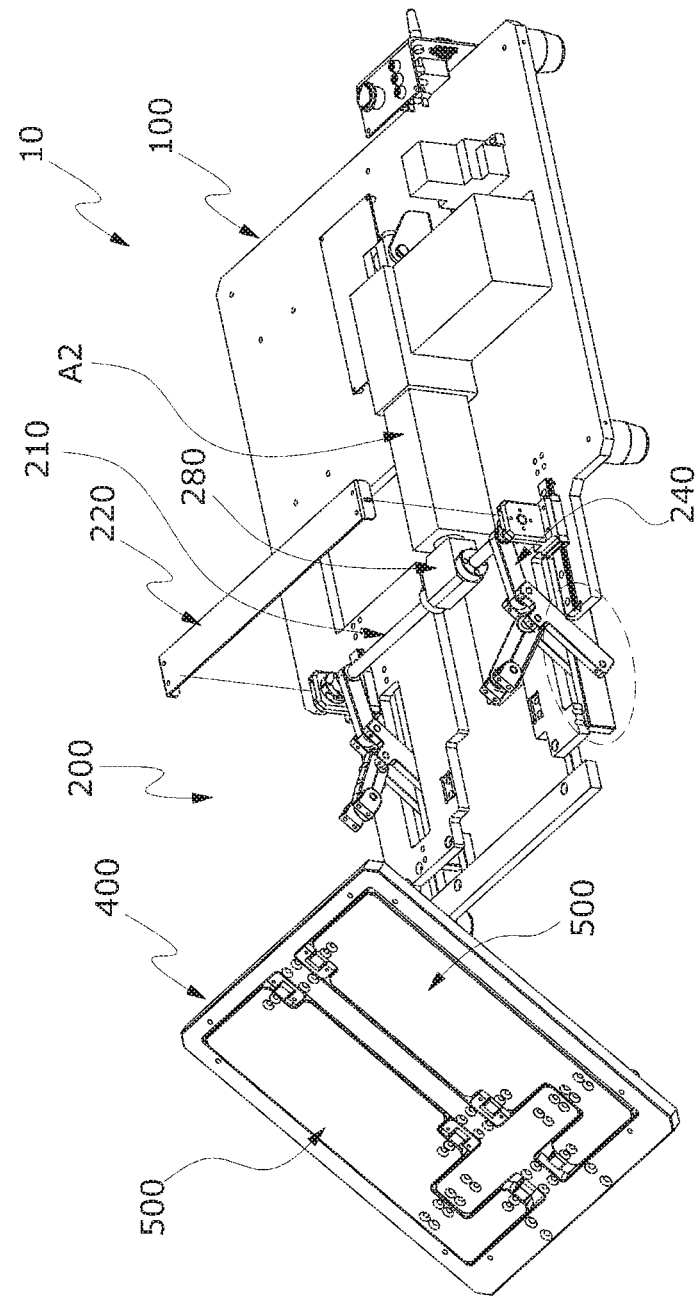
FIGS. 3(A and B) and 4 are exploded perspective views showing the second power transfer unit of a leg rehabilitation apparatus according to an embodiment of the present invention.
Figure 3B:
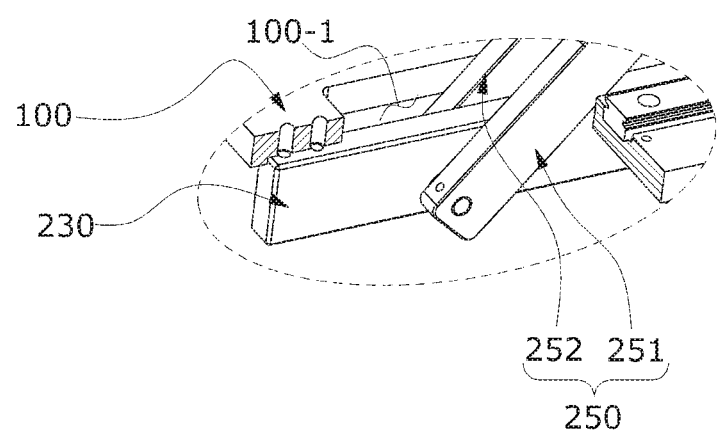
Figure 4:
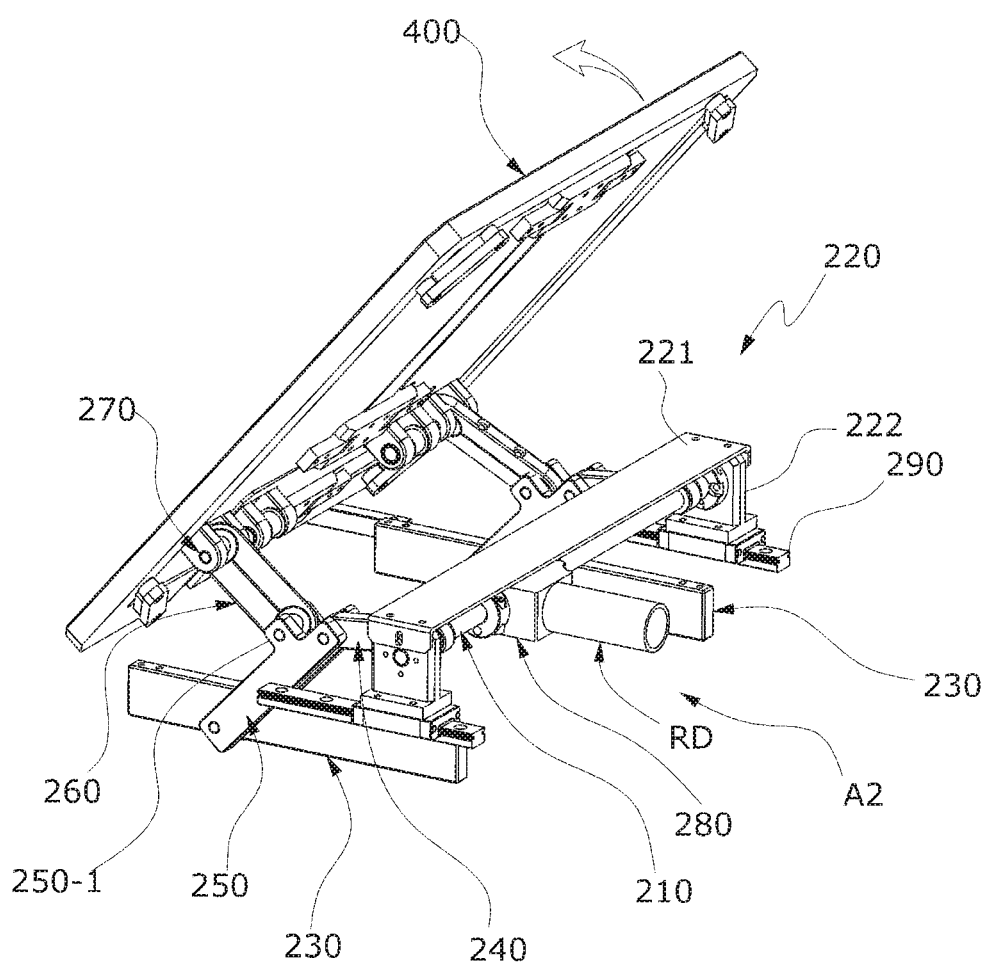

As shown in FIGS. 3(A and B) and 4, the second power transfer unit 200 includes a moving bar 210 moving forward to or backward from the second plate 500 by the second driving unit A1, a fixing bar 230 disposed in front or rear of the moving bar 210 and fixed to the base plate 100, and first to third link 250, 240 and 260 provided between the fixing bar 230 and the second plate 500.

The first link 250 has a bar shape and one side rotatably provided to the fixing bar 230. The second link 240 has a bar shape. The second link 240 has one side rotatably provided to the moving bar 210, and an opposite side rotatably provided to the first link 250. In addition, the third link 260 has a bar shape. The third link 260 has one side rotatably provided to a hinge 270 provided to the second plate 500, and an opposite side rotatably provided to the first link 250.

As shown in FIGS. 3(A and B) and 4, the fixing bar 230 is fixed to a low surface of the base plate 100. An opening part 100-1 is formed in the base plate 100 to which the fixing bar 230 is fixed to expose the fixing bar 230. The first link 250 is rotatably provided to the fixing bar 230.

The first link 250 is provided to the fixing bar 230 through the opening part 100-1. As shown, the first link 250 includes a pair of first link bars 251 and 252 pin-coupled to both sides of the fixing bar 230.

The second link 240 is rotatably provided to the first link 250. As shown in the drawings, a left side portion of the second link 240 is rotatably pin-coupled between the first link bars 251 and 252 of the first link 250. A right side portion of the second link 240 is rotatably pin-coupled to the moving bar 210.

The third link 260 is rotatably provided to the first link 250. As shown in the drawings, a right side portion of the third link 260 is pin-coupled to the first link 250. An additional coupling part 250-1 for coupling the third link 260 is provided to the first link 250. The right side portion of the third link 260 is pin-coupled to the coupling part 250-1. A left side portion of the third link 260 is pin-coupled to the hinge 270 provided to the second plate 500.

The moving bar 210 is reciprocated toward the second plate 500 (in direction 1) by the second driving unit A2.

The second driving unit A2 may be formed by using a hydraulic or air cylinder well known in the art. An operation rod RD reciprocated by the cylinder may be connected to the moving bar 210. As shown in the drawings, a moving block 280 may be provided to a central portion of the moving bar 210 and be connected to the operation rod RD to be reciprocated.

When the moving block 280 moves forward ahead to the second plate 500, the moving bar 210 interworking with the moving block 280 moves forward. When the moving bar 210 moves forward, the second link 240 moves forward in direction 3. The upper end of the first link 250 moves forward in direction 3 as the second link 240 moves forward, so that the third link 260 interworking with them moves forward. Since the hinge 270 is pressed in direction 3 due to the forward movement of the third link 260, as shown in FIG. 2, the second plate 500 is rotated about the first frame 410.

Since the sole of a user is placed on the second plate 500 rotated, due to the inversion and eversion movements of the sole, the ankle of the user may be rehabilitated.

The moving bridge 220 installed to the moving bar 210 to interwork with the moving bar 210 and the guide bar 290 fixed to the base plate 100 to guide the movement of the moving bridge 220 are provided to guide the movement of the moving bar 210.

The moving bridge includes support brackets 222 each provided outside two side ends of the moving bar 10 in a plate shape, and a bridge body 221 connected between the support brackets 222 and disposed at an upper side of the moving bar 210. That is, when the moving bar 210 moves, the moving bridge 220 interworking with the moving bar 210 moves.

The guide bar 290 is provided on the low surface of the support bracket 222. The guide bar 290 is disposed on the base plate 100 in the direction through which the moving bar 210 moves and is received in the support bracket 222 such that the guide bar 290 is coupled to the support bracket 222. Since the support bracket 222 moves while the guide bar 290 is received in the support bracket 222 such that the guide bar 290 is coupled to the support bracket 222, the moving bar 210 is guided to move stably.

Figure 6:
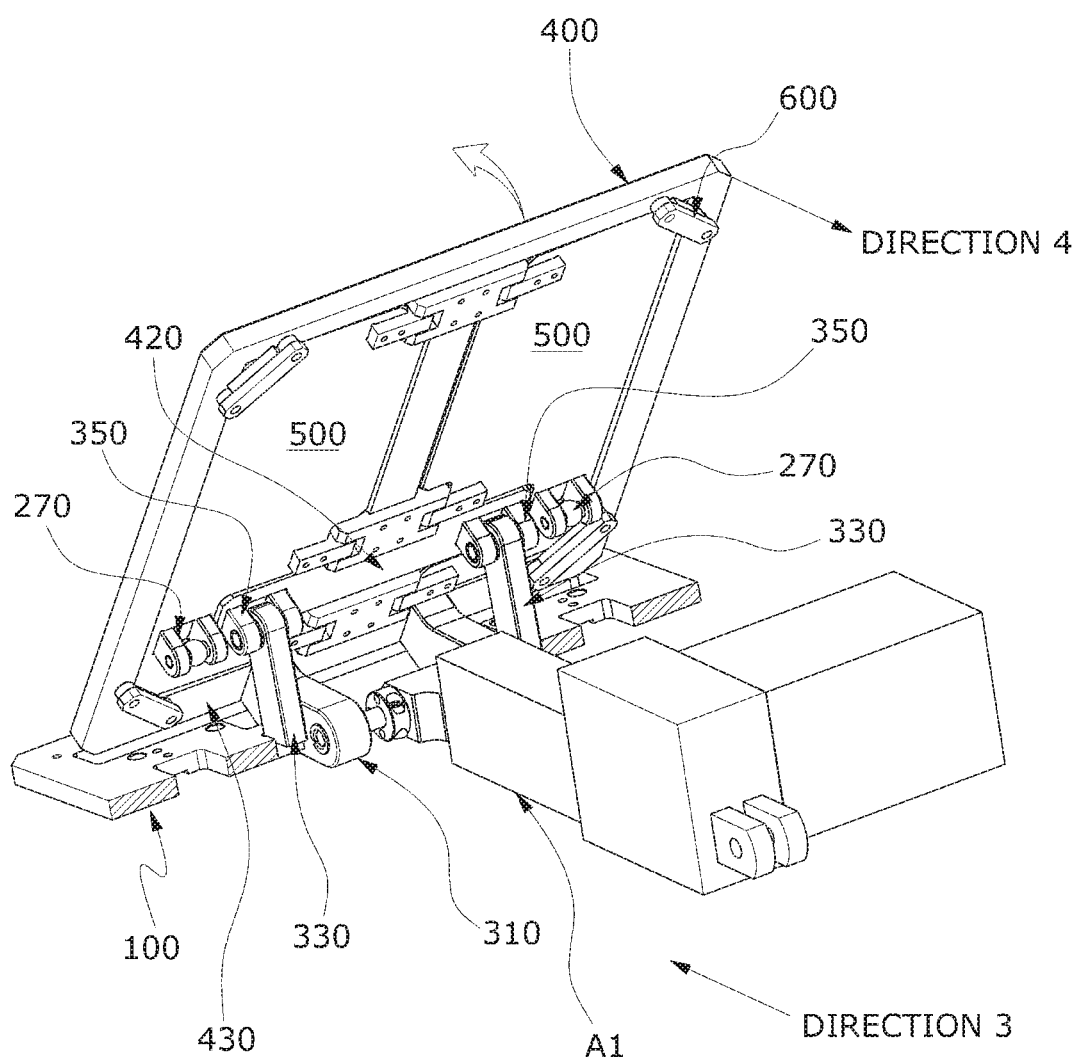

As shown in FIGS. 2A and 2B, the second plate 500 may be rotated to approach to the sole of the user and, as shown in FIG. 6, a stopper 600 is provided to prevent the second plate 500 from being rotated in the opposite direction. The stopper 600 is provided on the first plate 400 toward the driving unit A such that the second plate 500 may be prevented from being rotated toward the driving unit (in direction 4).

Figure 5:
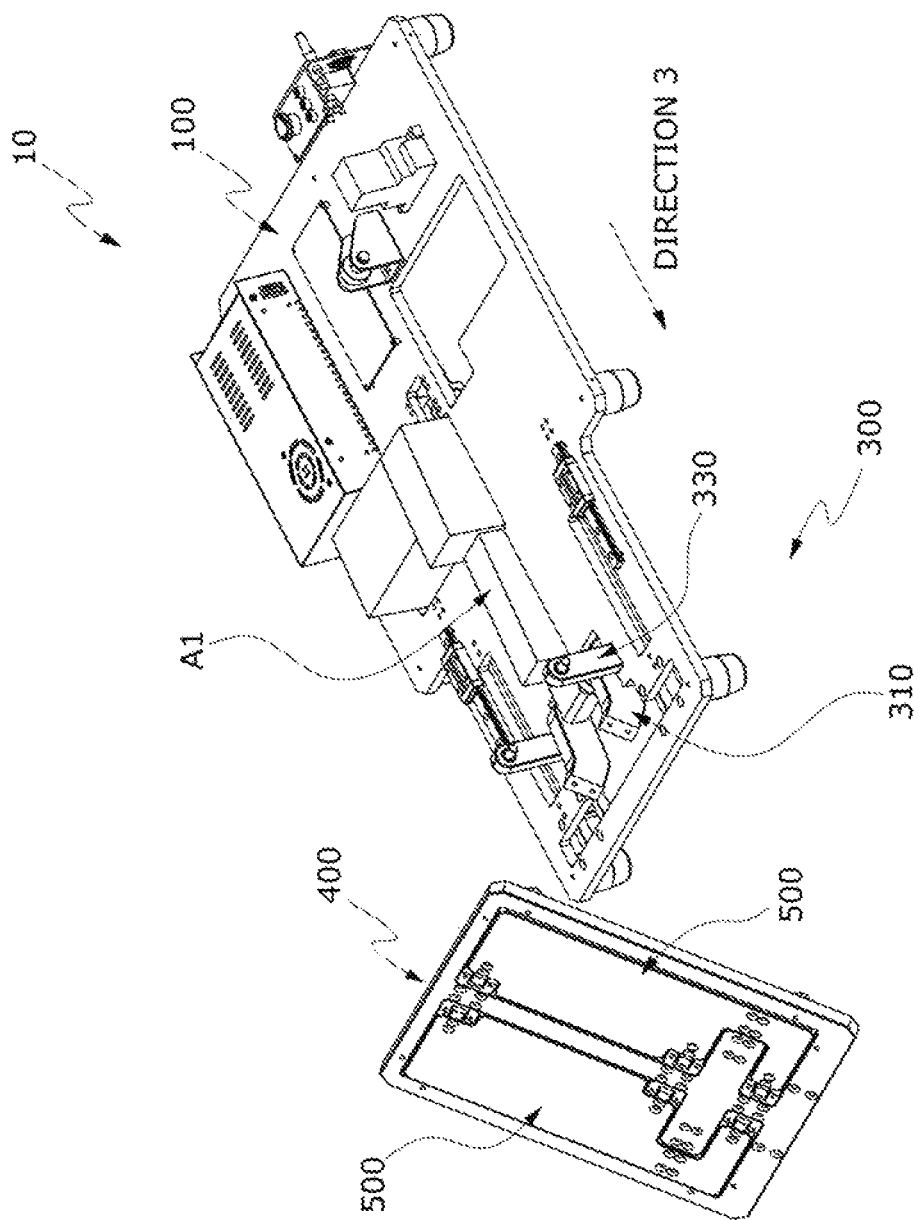
FIGS. 5 to 7 are exploded perspective views showing the first power transfer unit of a leg rehabilitation apparatus according to an embodiment of the present invention.
Figure 7:
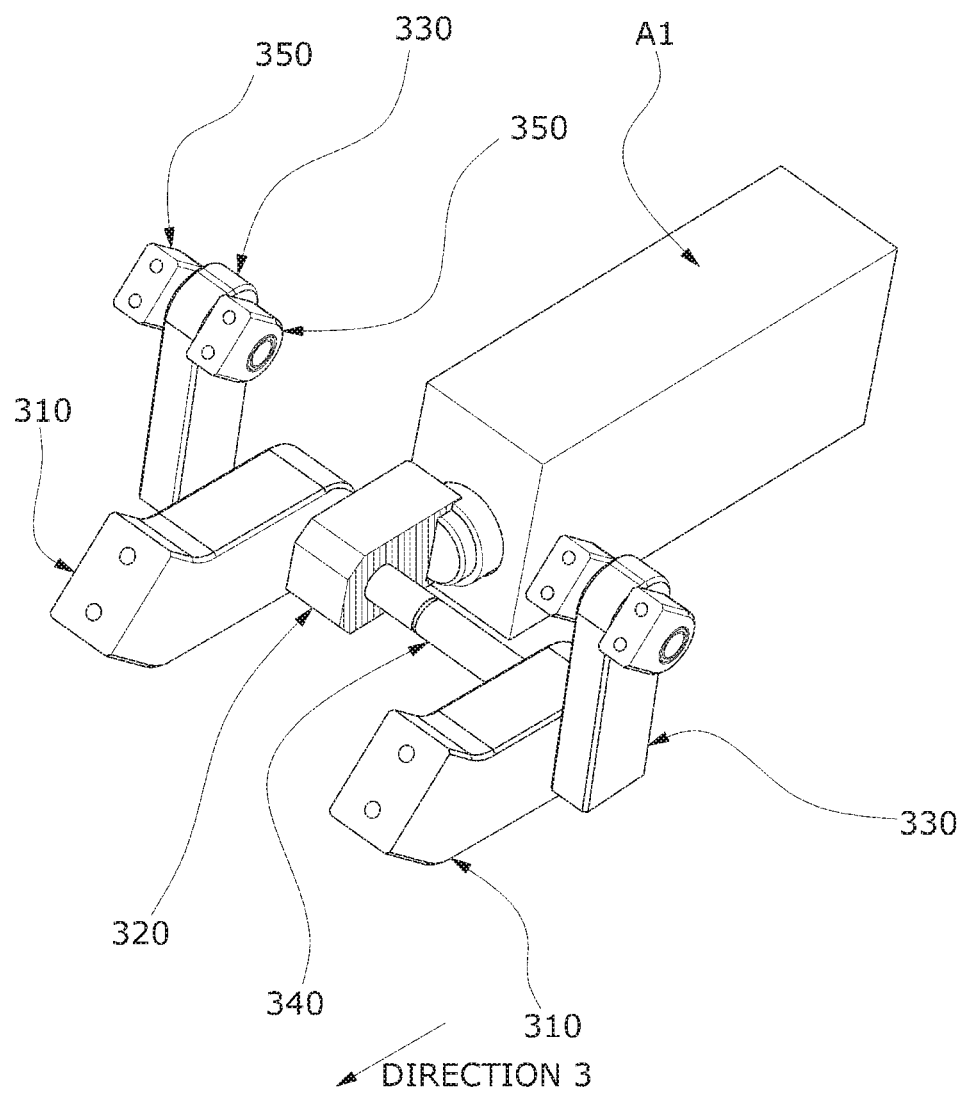

The first plate 400 is operated by the first power transfer unit 300. As shown in FIGS. 5 to 7, the first power transfer unit 300 includes a moving block 320 moving forwardly or backwardly toward the second plate 500 (in direction 3) by the first driving unit [A2]A1, a shaft 340 provided to the moving block 320 and disposed in a direction orthogonal to the moving direction of the first driving unit A1, and a connecting unit 310 having one side rotatably provided to the shaft 340 and an opposite side fixed to a low end of the outer frame 430 of the first plate 400.

In this case, a support bracket 330 is disposed between the base plate 100 and the second frame 420. As shown in the drawings, the left side portion of the support bracket 330 is rotatably provided to the hinge 350 installed to the second frame 420 of the first plate 400. The right side portion of the support bracket 330 is fixed to the base plate 100.

That is, when the moving block 320 moves forward in direction 3 by the first driving unit A1, the shaft 340 interworking with the first driving unit A1 moves forward, the connecting unit 310 presses a low end of the outer frame 430. Since the second frame 420 of the first plate 400 is rotatably fixed to the support bracket 330, the first plate 400 is rotated about the hinge 350.

Since the sole of a user is placed on the first plate 400 rotated, the toe part of the sole moves up or down due to such an operation, so that the ankle of the user may be rehabilitated.

Figure 8:
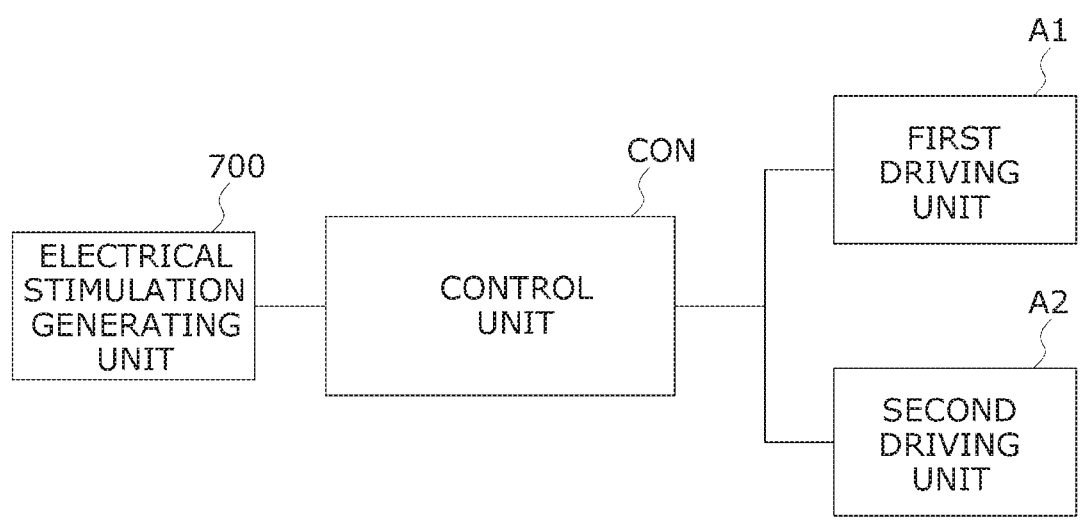
FIG. 8 is a conceptive view showing a control unit, a driving unit and an electrical stimulation generating unit of a leg rehabilitation apparatus according to an embodiment of the present invention.

As shown in FIG. 8, the apparatus may include a control unit CON connected to the driving unit A to control the driving unit A to stretch the ankle and the sole, and an electrical stimulation generating unit 700 connected to the control unit CON to apply electrical stimulation to a muscle of the leg under control of the control unit CON.

Since the electrical stimulation generating unit 700, which applies the electrical stimulation to a user by applying current, is well known in the art, the details will be omitted.

The control unit CON controls the electrical stimulation generating unit 700 and the driving unit A through a control signal. Since the configuration of the control unit CON is also well known in the art, the details will be omitted.

While an apparatus for rehabilitating a leg according to the present invention has been described with reference to preferred embodiments depicted in the accompanying drawings, those skilled in the art may change and modify the present invention in various ways without departing from the essential characteristic of the present invention. Therefore, the disclosed embodiments should be interpreted not in a limiting aspect but in a descriptive aspect. The scope of the invention is defined not by the detailed description of the invention but by the appended claims, and all differences within the scope will be construed as being included in the present invention.

What is claimed is:

1. An apparatus for rehabilitating a leg, the apparatus comprising:
    a base plate for supporting a patient;
    a first plate installed to the base plate and having a structure such that the first plate is rotatable to lift up a toe of the patient;
    a pair of second plates installed inside the first plate and rotatable to enable a sole of the patient to perform inversion and eversion movements and to allow a side surface of the sole to move up and down;
    a driving unit coupled to the first and second plates;
    a power transfer unit coupled to the first and second plates and the driving unit; and
    a control unit connected to the driving unit to control the driving unit to stretch an ankle and the sole,
    wherein the first plate comprises an outer frame having a hollow rectangular shape, a first frame for connecting central portions of mutually facing sides of the outer frame to each other to form openings at two sides thereof, a second frame extending from the first frame toward two sides of the first plate in an orthogonal direction to the first frame,
    wherein the two sides of the first frame each are connected to one of said pair of second plates, respectively, by a rotational part;
    wherein each of the second plates are disposed in a respective one of said openings;
    wherein the rotational part of each of the two sides comprises a hinge fixed to the first frame and a fixing bar rotatably coupled to the hinge, and wherein each of the pair of second plates are fixed to the fixing bar.

2. The apparatus of claim 1, wherein the power transfer unit comprises a second power transfer unit coupled to each second plate, and a first power transfer unit coupled to the first plate, and
    wherein the driving unit comprises a second driving unit coupled to the second power transfer unit and a first driving unit coupled to the first power transfer unit.

3. The apparatus of claim 2, wherein the second power transfer unit comprises a moving bar moving forward to or backward from the second plate by the second driving unit;
    a fixing bar disposed in front or rear of the moving bar and fixed to the base plate;
    a first link having one side rotatably provided to the fixing bar;
    a second link having one side rotatably provided to the moving bar, and an opposite side rotatably provided to the first link; and
    a third link having one side rotatably provided to a hinge provided to the second plate, and an opposite side rotatably provided to the first link.

4. The apparatus of claim 3, wherein the second power transfer unit further comprises a moving bridge installed to the moving bar to interwork with the moving bar, and a guide bar fixed to the base plate to guide a movement of the moving bridge,
    the moving bridge comprises support brackets each provided outside two side ends of the moving bar in a plate shape, and a bridge body connected between the support brackets and disposed at an upper side of the moving bar, and
    the guide bar is disposed on the base plate in a direction through which the moving bar moves and is received in the support bracket such that the guide bar is coupled to the support bracket.

5. The apparatus of claim 2, wherein the first power transfer unit comprises: a moving block moving forwardly or backwardly toward the second plate by the first driving unit;
    a shaft provided to the moving block and disposed in a direction orthogonal to the moving direction of the first driving unit;
    a connecting unit having one side which is rotatably provided to the shaft and an opposite side fixed to a low end of an outer frame of the first plate: and a support bracket having one side fixed to the base plate and an opposite side rotatably provided to a hinge installed to the second frame of the first plate.

* * * * *